United States Patent [19]

McMorrow

[11] Patent Number: 5,592,941
[45] Date of Patent: Jan. 14, 1997

[54] APPARATUS AND METHOD FOR NON-INVASIVELY DETECTING URINARY TRACT INFECTION USING ULTRASOUND

[75] Inventor: Gerald J. McMorrow, Kirkland, Wash.

[73] Assignee: Diagnostic Ultrasound Corporation, Redmond, Wash.

[21] Appl. No.: 546,068

[22] Filed: Oct. 20, 1995

[51] Int. Cl.$^6$ ........................................................ A61B 8/00
[52] U.S. Cl. ................ 128/660.07; 128/916; 128/662.02
[58] Field of Search .......................... 128/660.02, 660.07, 128/661.02, 661.1, 662.02, 916; 73/610, 861.25

[56] References Cited

U.S. PATENT DOCUMENTS 4,852,578  8/1989  Companion et al. .
4,926,871  5/1990  Ganguly et al. .
5,235,985  8/1993  McMorrow et al. .
5,363,850  11/1994  Soni et al. ............................ 128/662.02

*Primary Examiner*—George Manuel
*Attorney, Agent, or Firm*—Jensen & Puntigam, P.S.

[57] ABSTRACT

An ultrasound signal is transmitted into the center of the bladder. The received backscatter information is gated so that the data which remains is from a sample volume within the bladder and does not include information from the front or back walls and surrounding tissues of the bladder. The backscatter information is then compared with a preestablished threshold value. If the received backscatter is above a threshold value, it is indicative of a possible urinary tract infection, and an alarm is transmitted to the user.

14 Claims, 3 Drawing Sheets

APPARATUS AND METHOD FOR NON-INVASIVELY DETECTING URINARY TRACT INFECTION USING ULTRASOUND

TECHNICAL FIELD

This invention generally concerns body condition monitoring apparatus and more specifically concerns ultrasound monitoring of the condition of urine in the bladder as a way of detecting possible urinary tract infections.

BACKGROUND OF THE INVENTION

Bladder dysfunction is associated with frequent incidents of urinary tract infection. A person with bladder dysfunction, due to injury, disease, or other cause, is unable to readily detect a possible infection; accordingly, such persons are at high risk for urinary infections. Other persons also may have a high risk of urinary tract infection, due to other causes. There is now available non-invasive means for detecting the volume of urine in the bladder, which has been quite helpful for those persons with bladder dysfunction, due to which the fullness of the bladder cannot be physically detected by the person.

Such non-invasive means are shown in U.S. Pat. No. 4,926,871 to Ganguly et al. and U.S. Pat. No. 5,235,985 to McMorrow et al. However, those devices are only capable of detecting urine volume in the bladder, and are not directed toward detection of possible infection. For those persons at high risk for urinary tract infection, especially those with significant bladder dysfunction, it would be desirable to have an early warning of impending urinary tract infection, i.e. an ability to detect infection at an early stage, at which point it can be more readily and inexpensively treated.

DISCLOSURE OF THE INVENTION

Accordingly, the invention is an apparatus for detecting urinary tract infection comprising: ultrasound means for transmitting an ultrasound signal into a portion of the bladder; means for receiving a return "echo" signal from the bladder; means for gating the received echo signal so that only backscatter values from urine present in a sample volume within the bladder, excluding backscatter values from the bladder walls, remain; and means for comparing said sample volume backscatter values with a preestablished threshold value, wherein a backscatter value above the threshold is indicative of the presence of elements in the urine which in turn are indicative of a urinary tract infection.

BEST MODE FOR CARRYING OUT THE INVENTION

The present invention provides an early detection capability of urinary tract infection using ultrasound. In the absence of any infection, urine in the bladder is primarily sterile water, with a small amount of dissolved chemicals such as urea, as well as a small number of cells which have sloughed off the wall of the bladder itself. The scattering cross-section of normal urine is thus quite low. The tissue comprising the bladder wall and surrounding the bladder on the other hand has a high cellular concentration. Those cells have a nucleus which results in a very high scattering cross-section.

Certain bladder volume devices which detect the amount of urine in the bladder utilize this contrast in echogenicity between the urine and the bladder wall and surrounding tissue to make accurate determinations of bladder volume (the amount of urine in the bladder) in a non-invasive manner. Two such approaches are shown respectively in U.S. Pat. No. 4,926,871 to Ganguly and U.S. Pat. No. 5,235,985 to McMorrow et al., both of which are either owned or exclusively licensed by the assignee of the present invention. Both of those patents are hereby incorporated by reference. They provide detailed explanations of an ultrasonic transducer which is designed to transmit, receive and process ultrasound signals relative to the bladder and then to calculate bladder volume therefrom. Accordingly, the details of such ultrasound apparatus and calculations are not provided herein.

As indicated above, normal urine has a very low scattering cross-section. When there is a urinary tract infection, however, additional cells are typically present in the urine, including additional bladder wall cells as well as kidney cells, bacteria cells, red and white blood cells and occasionally even crystals which are caused by urea-splitting organisms such as proteus. While the "infected" urine still has a low echogenicity relative to the bladder wall and surrounding tissue, the echogenicity of infected urine is differentiated from that of normal urine. The applicants have understood and taken advantage of the full implications of this particular fact in their development of the present invention, which distinguishes between the echogenicity of normal urine and that of infected urine due to the bacteria and other cellular material in the infected urine, which causes an increase in the scattering of the ultrasound energy.

Figure 1:
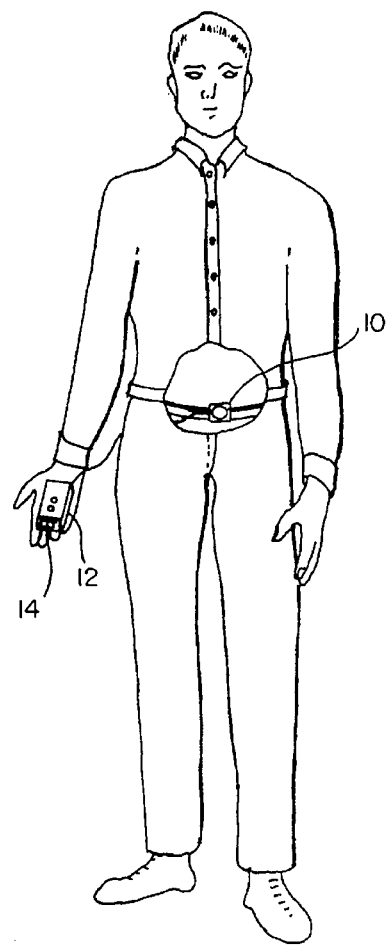
FIG. 1 is a diagram showing use of the present invention on a patient.

The apparatus as shown in FIG. 1 includes an ultrasound transducer member 10 which is held against the body adjacent the bladder. Transducer 10 can be held by strings or a belt 11 or can be held in a pocket on custom undergarments. The transducer 10 which transmits and receives the ultrasound signal is connected to a control processor unit 12. The control processor unit 12 contains the ultrasound processing electronics (microprocessor) and software, and also may include a readout portion 14 which provides a visual indication to the user concerning the fullness of the bladder. The control processor unit 12 also provides a visual/oral alarm when an indication of urine infection is determined.

Figure 2:
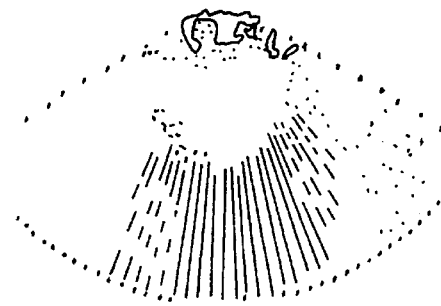
FIG. 2 is an ultrasound diagram of a bladder in one scan plane.

The transducer 10 is conventional and in operation transmits a 2.00 MHz sinusoid signal into the bladder region. The transmitted signal is shown in part A of the signal diagram of FIG. 4. In the embodiment shown, the ultrasound signal is transmitted in 5 microsecond bursts which each include ten complete cycles of the 2.0 Mhz signal. The 5 microsecond bursts occur every 256 microseconds during the scan sequence in the embodiment shown. The transducer is mounted so that it can sweep through successive planes in the bladder, with each plane comprising approximately 95 individual lines or signal bursts. After one plane of ultrasound signals is transmitted, such as shown in FIG. 2, the transducer is rotated through a small angle and another plane of signals is transmitted slightly rotated from the first plane. In the embodiment shown, a total of 12 planes of data are generated over an angle of 180°. One sweep or plane of ultrasound signals is illustrated in FIG. 2.

It should be understood, however, that the specific frequency of the ultrasound signal, the particular plane pattern of scanning the bladder, and the number of planes described herein are for illustration only and do not limit the scope of the present invention.

Using the returning reflected signal information from the transmitted ultrasound signal, the volume of the bladder is first calculated. This is described in detail in the '871 and '985 patents. From the bladder volume information, which may be displayed on readout 14 if desired, the centerline of the bladder, which presumably is the longest dimension between opposing walls, is determined. The dimensions of a "sample volume" are then established between the front and back walls of the bladder along the centerline, for the purpose of measuring the backscatter of the urine in the bladder.

Normally, the backscatter of the urine is so low that it is below the noise threshold of the ultrasound processing apparatus. This is because the returning reflected signal from the front and back walls of the bladder are both so much higher than the returning signal from the urine and because the very low amplitude backscatter of the urine has heretofore been of little, if any, interest. In the present invention, however, there is no interest in the backscatter information from the bladder walls and surrounding tissue.

Figure 3:
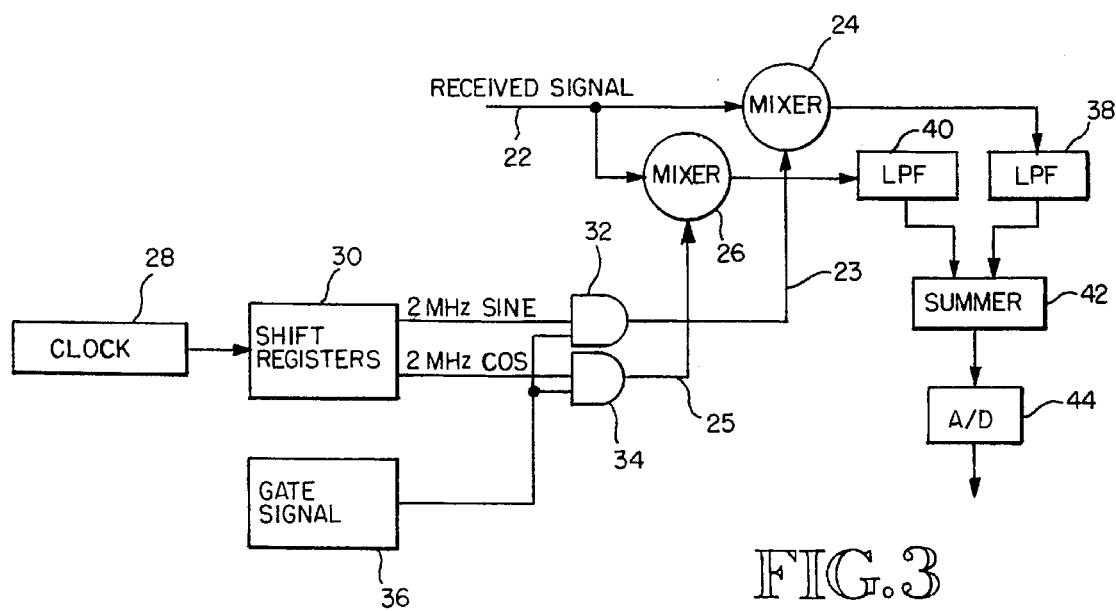
FIG. 3 is a block diagram of the processing circuitry of the present invention.
Figure 4A:
FIGS. 4A–4G are timing diagrams for the signal processing carried out in the present invention.
Figure 4B:
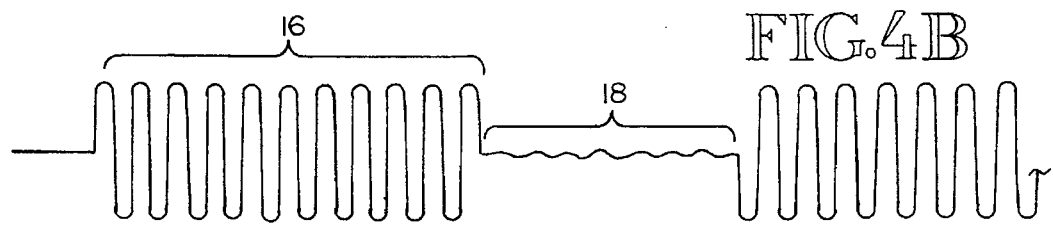

The "sample volume" information is achieved by eliminating what would otherwise be returning information from the front and back wall tissue. This is done by a time gating and quadrature processing arrangement which is shown in the block diagram of FIG. 3. The transmitted signal is shown in FIG. 4A. The return signal, sometimes referred to as an echo signal, is shown in FIG. 4B of the timing signal diagrams. The first 30 to 50 microseconds of the return signal, portion 16 in FIG. 4B, is return information from the front wall of the bladder and surrounding tissue. Following the front wall return information is the urine backscatter information 18, which typically lasts for approximately 50–60 microseconds, the distance between the front and back walls of the bladder. It is within this section that the "sample volume" of the urine in the bladder is established. Following the urine backscatter information, return information from the back wall and surrounding tissues of the bladder is received, shown as portion 20 in FIG. 4B.

The return signal undergoes processing to isolate the urine backscatter information. Referring to FIG. 3, the return signal is applied on line 22 as one input to two identical mixers 24 and 26. Applied as the other input to mixers 24 and 26, on lines 23 and 25, respectively, are 2.00 MHz square wave clock signals. The two clock signals have a sin/cosine (quadrature) relationship, i.e. 90° out of phase. These 2.00 MHz signals are produced by a 8.0 Mhz clock 28; shift registers 30 produce the 2.00 MHz sine and cosine quadrature signals. These signals are gated on and off through AND gates 32 and 34 by a gate signal source 36. The gate signal is high for a selected portion 37 of the return signal which is within the sample volume in the bladder, which in the embodiment shown is selected to be 5–20 microseconds, depending on the determined size of the bladder (the length of the centerline). A typical sample volume might be 4 cm. long for a bladder having a diameter of 6.6 cm. Such a sample volume would require a signal band width of approximately 40 KHz. This use of narrowband signals permits measurement of the backscatter from the urine.

Figure 4C:
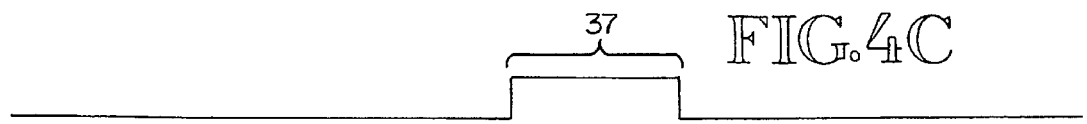
Figure 4D:
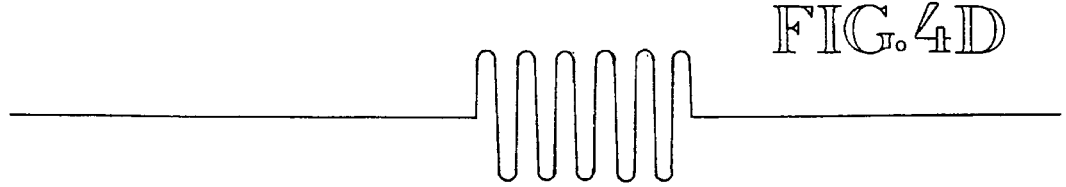
Figure 4E:
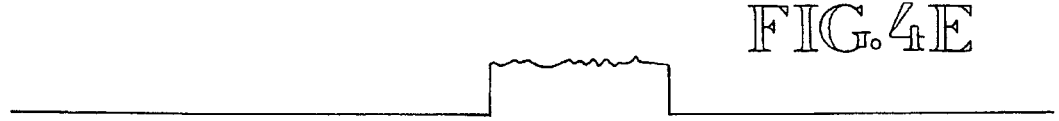
Figure 4F:

The gate signal and the gated clock signal outputs from AND gates 32 and 34 are shown in FIGS. 4C and 4D, respectively. These gated quadrature signals are then applied to mixers 24 and 26, as indicated above. The output of mixer 24 is shown in FIG. 4E while the output of mixer 26 is shown in FIG. 4F. The outputs from the mixers 24 and 26 thus include sum and difference signals, including backscatter data from only the sample volume within the bladder.

Figure 4G:

The outputs of the two mixers are applied, respectively, to low pass filters 38 and 40. The low pass filters eliminate the 2.00 MHz ultrasound signal. The resulting low frequency urine backscatter amplitude information within the sample volume from each mixer is applied to a summing circuit 42. The output of the summing circuit is then applied to an analog-to-digital converter 44, which produces digital information concerning the amplitude of the urine backscatter. The summed signal is shown in FIG. 4G.

Before the device is capable of producing an alarm, however, indicative of a potential infection, a threshold must be established for each individual user. Upon initial use of the apparatus, when the user is known to be free of infection, every time the bladder volume is measured, such as for instance, every ten minutes, the resulting data is stored, to develop a trend. In the thresholding process, urine backscatter in the form of a number is obtained. The backscatter information numbers are accumulated for approximately one week in order to establish a base line or threshold of data. The "mean" or mid-point of the accumulated trend information is then established. The absolute or maximum variance of all the individual data points relative to the mean is then determined (referred to as standard deviation), with the variance then being multiplied by a factor of 2.5. The mean value plus 2.5 times the variance is the data threshold for the instrument of the present invention for a particular user. It should be understood, however, that other threshold determinations could be used.

After the threshold value is obtained from this initial week or so of trend data, the instrument thereafter begins to make trend decisions, i.e. backscatter values are compared against the threshold. If the urine backscatter determinations during a particular period of time, such as four hours, indicates consistent backscatter values above the threshold, then an alarm is produced, which may be oral or visual on the readout. This warns the user of a possible or impending infection.

The user can use this information to notify their doctor, who can make a decision on treatment. If an infection is indicated, hopefully the indication will have been achieved at an early stage, and the infection can be remedied quickly through a minimum use of appropriate antibiotics or other measures, preventing the infection from becoming advanced and reducing recovery time significantly.

As can be seen, however, it is important to establish an accurate threshold which is the base line for a particular patient for normal urine reflectivity. It must not be too high, or the purpose of the device will be thwarted; also, it must not be too low or false indications of infection will result. To the best of applicant's knowledge, the above threshold formula produces good results.

Figures 5A, 5B:
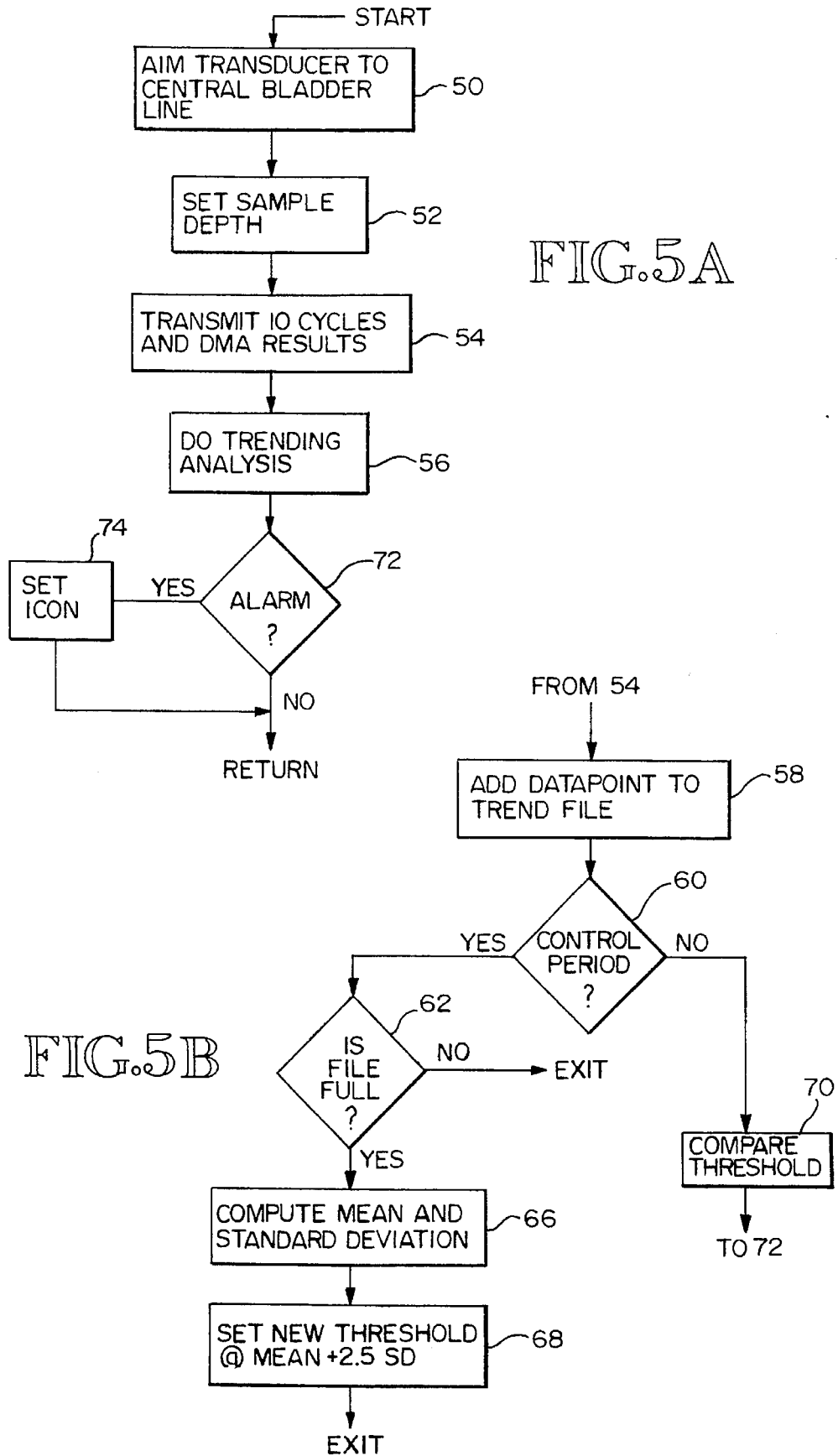
FIGS. 5A and 5B are flow charts for the software used to control the operation of the present invention.

The processing of the transmitted and received signal is carried out by a computer program, a flow chart of which is shown in FIGS. 5A and 5B. Referring now to FIG. 5A, the first step 50 is the aiming of the transducer to the bladder centerline, following the previous determination of bladder volume and bladder centerline, to obtain information from the sample volume within the bladder. The length (depth) of the sample volume within the bladder is then established, as shown in block 52, which is determined by the size of the bladder (previously determined) and which in turn determines the length of the gate signal. In block 54, ten cycle bursts of a 2.00 MHz ultrasound signal are transmitted into the bladder and the return signal from within the sample volume is received.

Block 56 in FIG. 5A concerns the development of the trending analysis and establishment of the threshold, followed by subsequent actual backscatter comparisons. Block 56 in FIG. 5A is shown in more detail in FIG. 5B. Each backscatter datum is initially added to a trend file as shown at block 58. If the data is received within the control period, i.e. the first week, as indicated by block 60 (Yes), the program then determines whether or not the trend file is full to the point of making a threshold determination (block 62). If not, then a threshold comparison is not made at that point, and the program is exited, to await the next datum. When the file is full, then the mean and variance (standard deviation) values are determined, as shown at block 66. The threshold is then established at a value of mean plus 2.5 the maximum variance, as shown at block 68. The program is then exited.

Once the threshold is established, and the program is outside the control period, then each new datum is compared against the threshold, as shown at block 70. An alarm decision is then made, as shown by block 72 in FIG. 5A. If an alarm is indicated, a icon (warning) is set, as shown by block 74, which as indicated above may be oral or visual, or some other signal recognizable to the user. If an alarm is not indicated (the NO leg from block 72) then the program goes back to start and awaits the next sample volume datum. New thresholds can be established by the user by resetting the device, although as a practical measure, once accurate, representative thresholds are obtained, there would be little, if any, advantage in having new thresholds.

Hence, applicant has produced a device which is capable of providing an early indication of possible urinary tract infection, by use of non-invasive ultrasound. The device can be worn comfortably by the user without significant public notice. The device provides authoritative information concerning the early onset of urinary tract infection. The user can then contact his/her doctor to eliminate the infection with minimal measures.

Although a preferred embodiment of the invention has been disclosed herein for illustration, it should be understood that various changes, modifications and substitutions may be incorporated in such embodiment without departing from the spirit of the invention which is defined by the claims which follow.

What is claimed is:

1. An apparatus for detecting urinary tract infection, comprising:

ultrasound means for transmitting an ultrasound signal into a portion of the bladder;

means for receiving a return signal from the bladder;

means for gating the received signal so that only backscatter values from urine in a sample volume in the bladder remain; and means for comparing said sample volume backscatter values against a pre-established threshold value, wherein a backscatter value above the threshold is indicative of the presence of elements in the urine which in turn indicate a urinary tract infection.

2. The apparatus of claim 1, including means for securing the ultrasound means to the person of a user.

3. The apparatus of claim 1, including means for determining an approximate centerline of the bladder and for transmitting the ultrasound signal along said centerline.

4. The apparatus of claim 1, wherein the gate signal permits passage of the return signal for a time duration in the range of 5–20 µseconds.

5. The apparatus of claim 1, wherein the gate signal begins to permit passage of the return signal at a selected time in the range of 30–50 µseconds following initial receipt of the return signal.

6. The apparatus of claim 1, including means for detecting the gated received signal with a synchronous quadrature detector.

7. The apparatus of claim 1, including means for providing an alarm to a user of the apparatus upon the threshold value being exceeded.

8. The apparatus of claim 1, including means for establishing the threshold value in accordance with backscatter values received from the user when there is no infection, wherein the threshold establishing means includes means for accumulating backscatter values over a selected period of time, establishing a mean value for said backscatter values and adding a multiple of a standard deviation value to the mean value.

9. An apparatus of claim 8, wherein the standard deviation is the maximum difference between the threshold establishing backscatter values and the mean value over the selected period of time and the multiple is approximately 2.5.

10. A method for detecting urinary tract infection, comprising:

transmitting an ultrasound signal into a portion of a bladder of a person;

receiving a return signal from the bladder;

gating the received signal so that only backscatter values from urine in a sample volume in the bladder remain; and comparing the sample volume backscatter values against a pre-established threshold value, wherein a backscatter value above the threshold is indicative of the presence of elements in the urine which in turn indicate a urinary tract infection.

11. The method of claim 10, wherein the transmitted signal is transmitted along a centerline of the bladder and wherein the sample volume is established about said centerline between front and back walls of the bladder.

12. The method of claim 10, including the step of providing an alarm to a user of the apparatus upon the threshold value being exceeded.

13. The method of claim 10, including the step of establishing the threshold value in accordance with backscatter values received from the user when there is no infection, wherein the step of establishing includes the step of accumulating backscatter values over a selected period of time, establishing a mean value for said backscatter values and adding a multiple of a standard deviation value to the mean value.

14. A method of claim 13, wherein the standard deviation value is the maximum difference between the threshold establishing backscatter values and the mean value over the selected period of time and the multiple is approximately 2.5.

\* \* \* \* \*